US00PP15831P2

(12) United States Plant Patent
Olesen et al.

(10) Patent No.: US PP15,831 P2
(45) Date of Patent: Jul. 5, 2005

(54) COMPACT FLORIBUNDA ROSE PLANT NAMED 'POULAC010'

(50) Latin Name: *Rosa hybrida*
Varietal Denomination: POULac010

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 34 days.

(21) Appl. No.: 10/812,710

(22) Filed: Mar. 29, 2004

(51) Int. Cl.[7] ..... A01H 5/00
(52) U.S. Cl. ..... Plt./149
(58) Field of Search ..... Plt./148, 149, 107

*Primary Examiner*—Anne Marie Grunberg
*Assistant Examiner*—June Hwu

(57) ABSTRACT

A new garden rose plant of the compact floribunda class which has abundant, pink flowers and attractive foliage. This new and distinct variety has shown to be uniform and stable in the resulting generations from asexual propagation.

1 Drawing Sheet

Botanical classification: *Rosa hybrida.*
Variety denomination: 'POULac010'.

SUMMARY OF THE INVENTION

The present invention constitutes a new and distinct variety of garden rose plant which originated from a controlled crossing between a female parent 'POULmax', described and illustrated in U.S. Plant patent application Ser. No. 10/192,746 dated Jul. 9, 2002 and the unnamed male parent. The two parents were crossed during the summer of 1992 and the resulting seeds were planted in a controlled environment in Fredensborg, Denmark. The new variety is named 'POULac010'.

The new variety may be distinguished from its female seed parent, 'POULmax' by the following combination of characteristics:

1. While the seed parent 'POULmax' has a flower bud color of Red Group 46C to 47D the same of 'POULac010' is Red-Purple Group 58A to 58B.
2. While the seed parent 'POULmax' has a petal count of 18 to 22 petals the same of 'POULac010' is 40 to 45 petals.
3. While the seed parent 'POULmax' has a general tonality of Red Group 43C the same of 'POULac010' is Red-Purple Group 58C.

The new variety may be distinguished from its unnamed male pollen parent, by the following combination of characteristics:

1. While the pollen parent has flower tonality which is true red, 'POULac010' is Red-Purple Group 58D.
2. While the pollen parent has a larger flower bud size than that of 'POULac010'.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance.

This combination of qualities is not present in previously available commercial cultivars of this type, known to the inventors, and distinguish 'POULac010' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULac010' was selected in the spring 1993 by the inventors as a single plant from the progeny of the aforementioned hybridization.

Asexual reproduction of 'POULac010' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULac010' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac010'. Specifically illustrated in SHEET 1:

FIG. 1.1; Open flower, and cluster of open flowers, showing branching, and the attachment of leaves, buds, and peduncles;

FIG. 1.2; Sepals, peduncles, receptacles;

FIG. 1.3; Flower petals, detached;

FIG. 1.4; Compound leaf;

FIG. 1.5; Bare stem exhibiting thorns.

DETAILED DESCRIPTION OF THE VARIETY

The following is a description of 'POULac010', as observed in its growth in a field nursery in Jackson County, Oreg. Observed plants were budded on to *Rosa multiflora* root stock and are 3 years of age. Color references are made using The Royal Horticultural Society (London, England) Colour Chart, 1995, except where common terms of color are used.

For a comparison, several physical characteristics of the rose variety 'POULmona', a rose variety from the same inventors described and illustrated in U.S. Plant patent application Ser. No. 10/211,119 dated Aug. 2, 2002, are composed to 'POULac010' in Chart 1.

CHART 1

| | 'POULac010' | 'POULmona' |
|---|---|---|
| General tonality | Red-Purple Group 58C | Red-Purple Group 58B |
| Petalage | 40 to 45 petals | 25 to 30 petals |
| Bud Color at ¼ open. | Red-Purple Group 58 A to 58 B | Red-Purple Group 58 B and C |
| Compound leaf measurements | 80 mm (1) × 45 mm (w) | 90 mm (1) × 75 mm (w) |

Parents:

*Female seed parent.*—'POULmax'.

*Male pollen parent.*—Unnamed plant.

FLOWER AND FLOWER BUD

Blooming habit: Continuous.

Flower bud:

*Size.*—Upon opening, 27 mm in length from base of receptacle to end of bud.

*Bud form.*—Pointed ovoid.

*Bud color.*—As sepals unfold, petals are Red-Purple Group 58A to 58B.

*Sepals.*—Upper surface: Color: Yellow-Green Group 144B to 144A. Surface: Moderately pubescent. Lower surface: Color: Yellow-Green Group 144B. Sepal shape: Sepal apex is cirrhose. Base is flat at union with receptacle. Sepal margin: Margins have no foliaceous appendages on three of the five sepals. Size: 21 mm(l)×7 mm (w).

*Receptacle.*—Surface texture: Smooth. Shape: Urn-shaped. Size: 6 mm (h)×6 mm (w). Color: Yellow-Green Group 144A.

*Pedicel.*—Surface: Smooth and glabrous. Length: 30 to 35 mm in length. Diameter: 2.5 mm. Color: Yellow-Green Group 144A. Anthocyanic intonations of Greyed-Orange Group 177A observed. Strength: Somewhat strong.

*Borne.*—In clusters of 5 flower buds per stem.

Flower bloom:

*Fragrance.*—Light floral scent.

*Duration.*—The blooms have a duration on the plant of approximately 7 to 10 days. After flowers have completely matured, petals fall cleanly away from plant.

*Size.*—Flower diameter is 55 mm when open. Flower depth is 28 mm on average.

*Form.*—General shape is a rosette with many overlapping petals of varied sizes.

*Shape of flower when viewed from the side.*—Upon opening, Upper part: flattened convex. Lower part: flattened convex. Open flower, Upper part: flat. Lower part: concave.

Petalage: 40 to 45 petals under normal conditions, 5 to 10 of which are petaloids.

Color:

Upon opening, petals:

*Outermost petals.*—Outer side: Red-Purple Group 58A to 58B. Inner side: Red-Purple Group 58C.

*Innermost petals.*—Outer side: Red-Purple Group 58B to 58C. Inner side: Red-Purple Group 58C.

Upon opening, basal petal spots:

*Outermost petals.*—Outer side: Yellow Group 5B. Inner side: Yellow Group 5B.

*Innermost petals.*—Outer side: Yellow Group 5B. Inner side: Yellow Group 5B.

After opening, petals:

*Outermost petals.*—Outer side: Red-Purple Group 58D with light intonations of Red-Purple Group 58B. Inner side: Red-Purple Group 58D.

*Innermost petals.*—Outer side: Red-Purple Group 58C to 58D with light intonations of Red-Purple Group 58B. Inner side: Red-Purple Group 58D.

After opening, basal petal spots:

*Outermost petals.*—Outer side: Yellow Group 5C. Inner side: Yellow Group 5C.

*Innermost petals.*—Outer side: Yellow Group 5C. Inner side: Yellow Group 5C.

General tonality: On open flower Red-Purple Group 58C. No change in the general tonality at the end of the 10th day.

Petals:

*Petal reflex.*—Somewhat reflexed.

*Margin.*—Entire and uniform.

*Shape.*—Apex: Round. Base: Acute.

*Size.*—Variable. Outer petals are 30 mm(l)×30 mm(w). Inner petals are 28 mm (l)×15 mm (w).

*Texture.*—Smooth.

*Thickness.*—Average.

*Arrangement.*—Not formal.

Petaloids:

*Quantity.*—10 to 15.

*Color.*—Upper Surface: Red-Purple Group 58D. Lower Surface: Red-Purple Group 58D.

*Size.*—23 mm (l)×15 mm (w).

*Shape.*—Apex is rounded. Base is acute.

Reproductive organs:

*Pistils.*—Length: 4 mm. Quantity: 35.

*Pollen.*—None observed.

*Anthers.*—Size: 2 mm in length. Color: Greyed-Yellow Group 162A. Quantity: 40 (actual count).

*Filaments.*—Color: Yellow Group 8A to 8B. Length: 6 mm.

*Stigmas.*—Inferior relative to the length of filaments and the height of the anthers. Color: Greyed-Yellow Group 160C.

*Styles.*—Length: 6 mm on average. Color: Greyed-Yellow Group 160C.

*Hips.*—None observed in the field nursery in Jackson County Oreg.

PLANT

Plant growth: Moderate, upright to bushy. When grown as a budded field grown plant on *Rosa multiflora* understock, the average height of the plant is 40 to 60 cm and the average width is 40 cm.

Stems:

*Color.*—Young wood: Yellow-Green Group 146C. Older wood: Yellow-Green Group 146C.

*Surface texture.*—Young wood: Smooth. Older wood: Rough.

Thorns:

Incidence.—14 thorns per 10 cm of stem.

*Size.*—Average length: 6 mm.

*Shape.*—Concave.

*Color.*—Mature thorns are Yellow-Green Group 146C. Juvenile thorns are Greyed-Orange Group 176A.

Plant foliage: Normal number of leaflets on normal leaves in middle of the stem: 5 to 7 leaflets.

*Compound leaf size.*—On average, compound leaves are 80 mm in length by 45 mm wide.

*Color.*—Mature Foliage: Upper surface is Yellow-Green Group 147A to 147B. Lower surface is Yellow-Green Group 146B. Juvenile foliage: Upper surface is Yellow-Green Group 144A with intonations of Yellow-Green Group 152A. Lower surface is Yellow-Green Group 144A with Yellow-Green Group 152A. Anthocyanic intonations the color of Greyed-Orange Group 173A observed. Anthocyanin: Location: New shoots and leaves. Color: Greyed-Orange Group 173A.

Plant leaves and leaflets:

*Stipules.*—Size: 25 mm in length. Quantity: 2 per compound leaf. Margins: Medium to average quantity of stipitate glands observed. Color: Yellow-Green Group 144A.

*Petiole.*—Length: 27 mm. Diameter: 2 mm. Color: Yellow-Green Group 144A to 144B. Anthocyanic intonations the color of Greyed-Red Group 181A observed. Underneath: Prickles. Observations: Few stipitate glands on upper surface.

*Rachis.*—Length: 35 to 40 mm. Color: Yellow-Green Group 144A to 144B. Underneath: Prickles. Observations: Few stipitate glands on upper surface.

*Leaflet.*—Margins: Doubly serrated. Size: Average size of the terminal leaflet on normal leaves 22 to 30 mm (l)×16 to 27 mm (w). Shape: Ovate to round. Leaflet base is cuneate. Leaflet apex is cuspidate. Arrangement: Odd pinnate. Venation: Reticulate. Texture: Smooth. Glossiness: Glossy.

Disease resistance: Above average resistance to mildew, rust, black spot, and *Botrytis* under normal growing conditions in Jackson County, Oreg.

Cold hardiness: The variety 'POULac010' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant pink, disease resistance, and extended period of bloom.

* * * * *

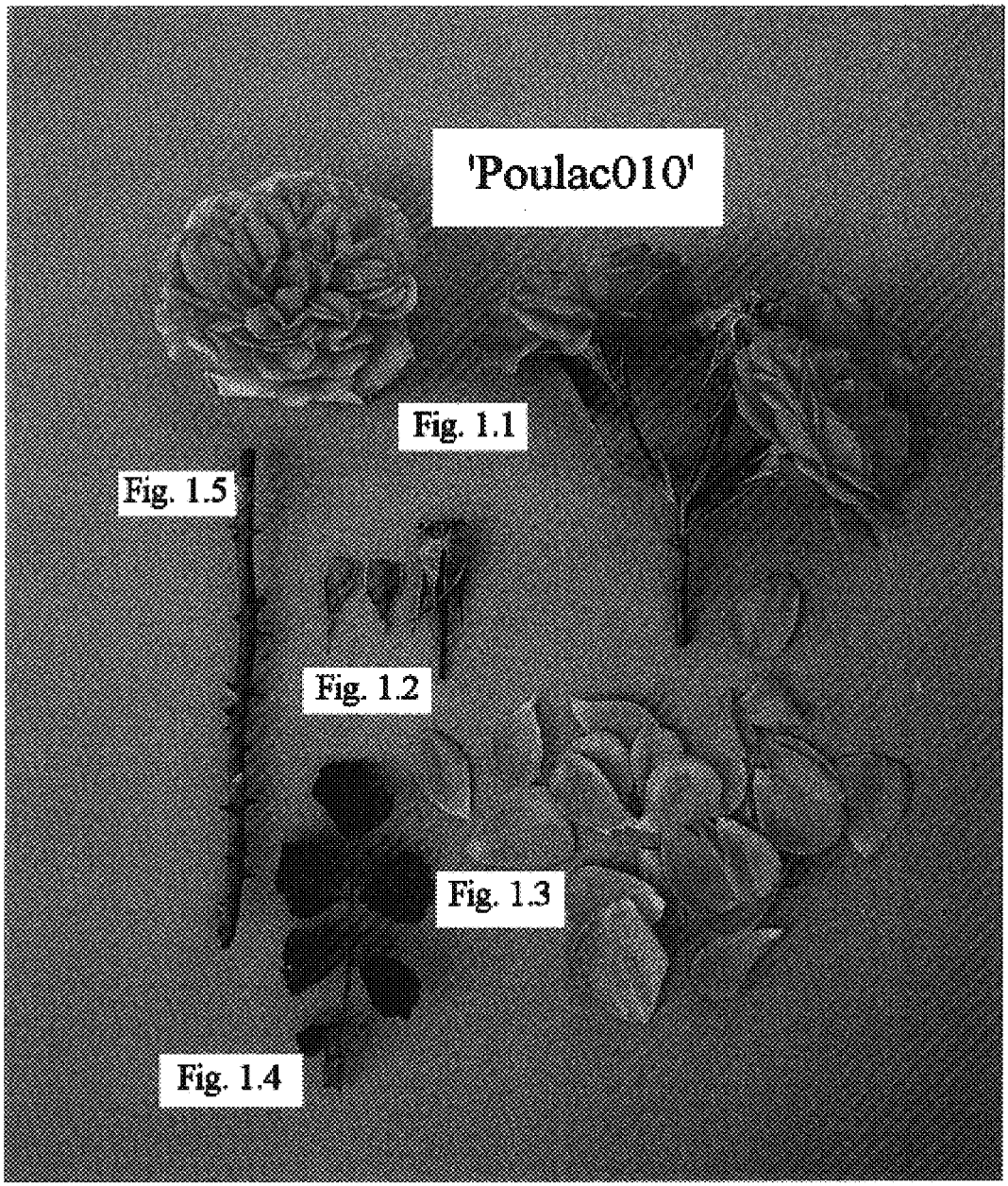
'Poulac010'
Fig. 1.1
Fig. 1.5
Fig. 1.2
Fig. 1.3
Fig. 1.4